United States Patent [19]

Grossman et al.

[11] 4,243,939
[45] Jan. 6, 1981

[54] DETERMINING PARAMAGNETIC ADDITIVE CONTENT OF A BASE PARAMAGNETIC MATERIAL CONTAINING FERROMAGNETIC IMPURITY

[75] Inventors: Leonard N. Grossman, Wrightsville Beach, N.C.; Alan M. Portis, Berkeley; Henry Bernatowicz, Menlo Park, both of Calif.; Frederick C. Schoenig, Jr., Wilmington, N.C.

[73] Assignee: General Electric Company, San Jose, Calif.

[21] Appl. No.: 931,670

[22] Filed: Aug. 7, 1978

[51] Int. Cl.² .............................................. G01R 33/16
[52] U.S. Cl. .................................... 324/201; 324/228; 324/239; 324/242
[58] Field of Search ............... 324/201, 217, 218, 222, 324/223, 228, 239, 240, 241, 242, 243, 260, 261, 262

[56] References Cited

U.S. PATENT DOCUMENTS 1,322,405  11/1919  Burrows .............................. 324/240

FOREIGN PATENT DOCUMENTS 2643664  3/1978  Fed. Rep. of Germany ........... 324/201
171639  10/1965  U.S.S.R. .................................. 324/228

*Primary Examiner*—Rudolph V. Rolinec
*Assistant Examiner*—Walter E. Snow
*Attorney, Agent, or Firm*—Ivor J. James, Jr.; Samuel E. Turner; Raymond G. Simkins

[57] ABSTRACT

Method and apparatus for the nondestructive determination of the amount and quantitative distribution of a paramagnetic additive such as gadolinia in nuclear fuel elements. Changes in paramagnetic susceptibility of the material in the element are detected as the element is passed through a constant magnetic field and compared to the changes in susceptibility produced by a standard element of known additive content.

33 Claims, 9 Drawing Figures

| ZONE NO. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PELLETS IN ZONE | 17 | 3 | 16 | 2 | 16 | 1 | 21 | 1 | 16 | 2 | 16 | 3 | 23 | 3 |
| Gd$_2$O$_3$ (%) | 2.0 | 1.0 | 2.0 | 1.0 | 2.0 | 1.0 | 2.0 | 3.0 | 2.0 | 3.0 | 2.0 | 3.0 | 2.0 | 2.1 |
| IRON (ppm) | 79 ±24 | 93 ±23 | 79 ±24 | 93 ±23 | 79 ±24 | 93 ±23 | 79 ±24 | 67 ±30 | 79 ±24 | 67 ±30 | 79 ±24 | 67 ±30 | 79 ±24 | 29 ±5 |

| ZONE INTERFACE NUMBER | 1/2 | 2/3 | 3/4 | 4/5 | 5/6 | 6/7 | 7/8 | 8/9 | 9/10 | 10/11 | 11/12 | 12/13 | 13/14 |
|---|---|---|---|---|---|---|---|---|---|---|---|---|---|
| PEAK VOLTAGE AT INTERFACE (mV) | −21 | +22 | −23 | +22 | −23 | +21 | +23 | −20 | +33 | −26 | +27 | −27 | −17 |

Fig. 7

| ZONE | LENGTH OF ZONE (cm) | MEASURED DENSITY | MEASURED GADOLINIUM WEIGHT PERCENT | TARGET GADOLINIUM WEIGHT PERCENT |
|---|---|---|---|---|
| 1 | 15.024 | 96.574 | 0.0 | 0.0 |
| 2 | 30.592 | 95.554 | 2.986 | 3.0 |
| 3 | 30.447 | 94.790 | 1.10 | 1.0 |
| 4 | 29.919 | 96.574 | 0.0 | 0.0 |
| 5 | 30.757 | 94.617 | 7.88 | 8.0 |
| 6 | 30.734 | 95.554 | 2.986 | 3.0 |
| 7 | 30.470 | 94.429 | 6.65 | 7.0 |
| 8 | 30.345 | 94.425 | 9.83 | 10.0 |
| 9 | 30.917 | 96.574 | 0.0 | 0.0 |
| 10 | 15.51 | 94.396 | 1.38 | 1.5 |
| 11 | 15.088 | 94.790 | 1.10 | 1.0 |
| 12 | 15.69 | 96.574 | 0.0 | 0.0 |
| 13 | 15.10 | 94.429 | 6.65 | 7.0 |
| 14 | 15.253 | 95.993 | 3.78 | 4.0 |
| 15 | 15.055 | 94.617 | 7.83 | 8.0 |
| 16 | 15.103 | 94.425 | 9.83 | 10.0 |
| 17 | 14.859 | 96.574 | 0.0 | 0.0 |

*Fig. 8*

DETERMINING PARAMAGNETIC ADDITIVE CONTENT OF A BASE PARAMAGNETIC MATERIAL CONTAINING FERROMAGNETIC IMPURITY

BACKGROUND OF THE INVENTION

This invention relates to fuel for nuclear reactors. Such nuclear reactors are discussed for example in "Nuclear Power Engineering", M. M. El-Wakil, McGraw-Hill Book Company, Inc., 1962.

Nuclear reactors are typically refueled periodically with an excess of fuel sufficient to maintain operation throughout an operating cycle.

This excess of fuel results in an excess of reactivity which requires a control system of sufficient strength to maintain the effective multiplication factor at unity during reactor operation. The control system customarily comprises neutron absorbing or poison materials that serve to control the neutron population by nonfission absorption or capture of neutrons. Typically, the control system includes mechanical control in the form of a plurality of selectively actuatable poison containing control rods or the like which can be inserted into and withdrawn from the core as required.

It is also known to include in the fuel core a burnable poison which is a strong neutron absorber but is converted by neutron absorption to an isotope of low control worth (neutron absorbing capacity). Such use of burnable poisons decreases the amount of mechanical control required and, by appropriate arrangement of the burnable poison, improvements in power distribution can be achieved thereby.

Such burnable poisons frequently are incorporated in the fuel core in a mixture with selected portions of the nuclear fuel. Such nuclear fuel is typically in the form of pellets or powder contained in an elongated cladding tube to form a fuel element as shown, for example, in U.S. Pat. No. 3,378,458. An arrangement of burnable poison in a fuel core is shown, for example, in U.S. Pat. No. 3,799,839.

It is desirable for quality control and identification purposes during nuclear fuel handling and manufacturing processes to have rapid nondestructive methods of determining the amount and location of the burnable poison in a nuclear fuel element. Since gadolinium is one of the most widely used burnable poisons, it is particularly desirable to determine the gadolinium content of nuclear fuel.

When an additive has a magnetic susceptibility sufficiently greater than the magnetic susceptibility of its admixed nuclear fuel, its susceptibility in a magnetic field can be measured to determine the location and amount of the additive in the fuel element.

Typical nuclear fuel, such as oxides of uranium and plutonium are paramagnetic. For example, the room temperature susceptibility of uranium dioxide ($UO_2$) is $8.76 \times 10^{-6}$ emu/g-Oe (electrmagnetic unit/gram-Oersted). Fortuitously, the room temperature susceptibility of gadolinia ($Gd_2O_3$) is significantly greater, namely, $147 \times 10^{-6}$ emu/g-Oe. This difference is sufficient to make practical the magnetic determination of gadolinium additive content in nuclear fuel.

A problem which complicates the magnetic determination of gadolinium or other paramagnetic additives in nuclear fuel is the presence of ferromagnetic impurities, such as iron, therein, typical fuel containing 100 ppm (parts per million) or more of such impurities. The susceptibility of such ferromagnetic impurities is very high in low magnetic fields but decreases greatly in high fields as they tend to become saturated.

Advantage is taken of this in a method and apparatus for magnetically determining the $Gd_2O_3$ content in $UO_2$ fuel pellets shown and described in U.S. patent application Ser. No. 754,581, filed 27 Dec. 1976, now U.S. Pat. No. 4,134,064. As therein described, the ferromagnetic inclusions are saturated with a high, constant magnetic bias field while the gadolinia content of the fuel is determined by measurement of the alternating current susceptibility using an inductive technique.

General information on magnetic materials and properties is given in Magnetism and Metallurgy, edited by A. Berkowitz and E. Kneller, Academic Press, New York, 1969.

OBJECTS

An object of the invention is the rapid, nondestructive determination of the distribution and content of an additive having a given paramagnetic susceptibility in a material having a significantly different paramagnetic susceptibility.

Another object is to determine the content and distribution of a paramagnetic additive in a material containing ferromagnetic impurities.

Another object is to eliminate the contribution of ferromagnetic material to the signals produced by magnetic susceptibility measurements of base paramagnetic material containing ferromagnetic impurities and a paramagnetic additive.

Another object is to measure the content and distribution of ferromagnetic material in a base paramagnetic material.

SUMMARY

In a first embodiment of the invention, susceptibility changes in a base paramagnetic material, such as nuclear fuel, containing a paramagnetic additive, such as burnable poison, are detected as the material is passed through a constant magnetic field, the signals due to susceptibility changes being compared to signals from known standards to determine the additive content. This embodiment of the invention is adapted for use where the base material contains an insignificant or known amount of ferromagnetic impurity.

In a second embodiment of the invention, the material, containing an additive and ferromagnetic impurities, is passed in series through two constant magnetic fields to different strengths and the differential susceptibility of the material in the two different magnetic fields is determined and processed to provide an indication of the additive content. Additionally or alternatively the ferromagnetic impurity content is similarly determined. This embodiment of the invention is useful where the amount of ferromagnetic impurity is unknown.

Also shown and described in a densitometer arrangement which may be added to correct the additive indicating signal for changes in material density and to detect voids.

DRAWING

FIG. 7 is a chart of data concerning the sample element of the example set forth herein in connection with FIG. 6; and FIG. 8 is a chart of data concerning an example fuel element tested with the apparatus of FIG. 5.

FIRST EMBODIMENT

Figure 1:
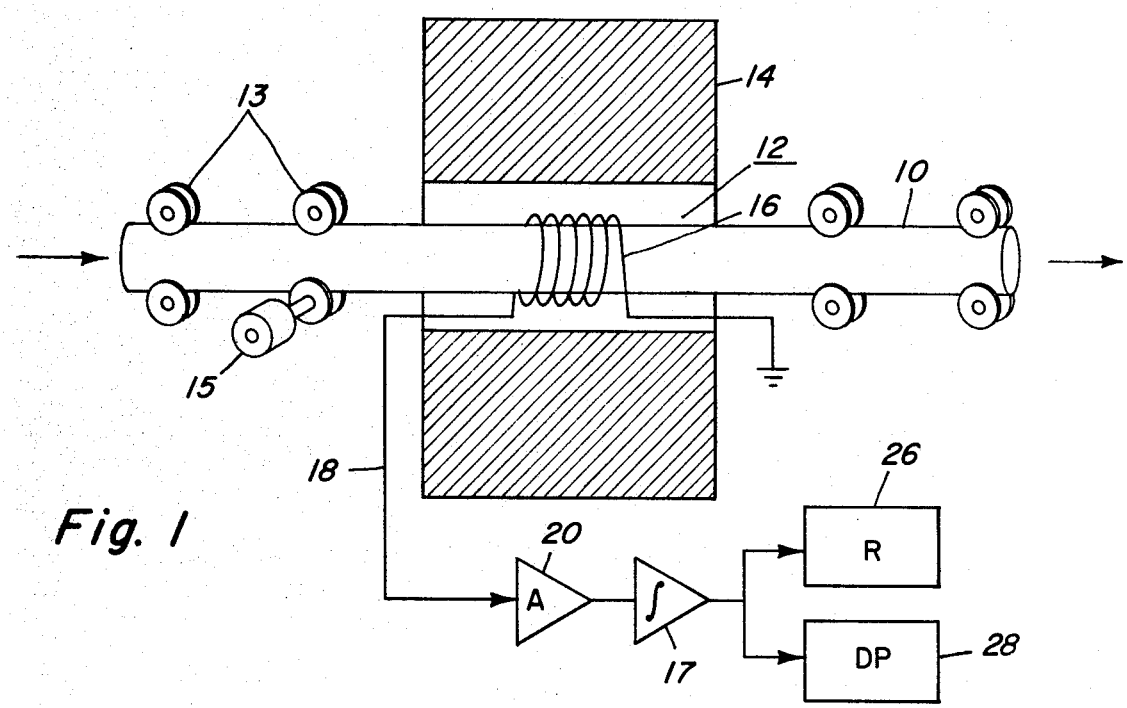
FIG. 1 is a schematic illustration including a magnet and associated circuitry in accordance with the first embodiment of the invention.

Shown in FIG. 1 is apparatus for determining the amount of a paramagnetic additive, such as gadolinium, in nuclear fuel which contains insignificant or known amount of ferromagnetic impurities such as iron.

A nuclear fuel element 10 contains the nuclear fuel and additive and is clad with a nonmagnetic material such as a zirconium alloy. The element 10 is moved through a sensing coil 16 positioned in the opening or bore 12 of an annular magnet 14 which produces a constant or direct current magnetic field. The element 10 may be driven and guided by suitable means such as four pairs of grooved wheels 13, one or more of which are driven by a motor 15. Thus a voltage is induced in coil 16 proportional to changes in magnetic susceptibility of the material in element 10 as it is moved through the coil. That is, the coil 16 produces a voltage V which is prportional to the product of the change in susceptibility of dX times N (the number of turns of coil 16) times H (the field strength of the magnet 14 in the region of the coil 16). The voltage developed by coil 16 is applied over a lead 18 to an amplifier 20 and thence to a well-known indicating and recording means such as a strip or chart recorder 26. If desired, the signal from amplifier 20 may be integrated in a well-known manner, for example, by a well-known integrating amplifier 17, as illustrated. The graph of the voltages recorded by the recorder 26 then may be compared to a graph of the voltages produced and similarly recorded from a standard fuel element containing known amounts of additives to determine the weight percent and distribution of the additive in element 10.

The signals from amplifier 20 also (or alternatively) may be applied to a well-known data processing device 28 wherein the signals automatically are compared to stored standards. The device 28 may provide a readout of the amount and axial location of the additive and/or provide an indication that the fuel material is within or outside of predetermined specifications.

For high sensitivity the sensing coil 16 should comprise a large number of turns (e.g. 1000) consistent with the space available in the bore 12 and with minimization of resistance of the winding. Preferably the winding of coil 16 occupies the center of the length of the bore 12 (in the region of highest field strength) and has the minimum inside diameter necessary to pass reliably the element 10.

The element 10 should be moved through the coil 16 at a constant velocity, within about plus or minus 0.1 percent, in the range of from 1 to about 100 feet per minute, the preferred range being 15 to 40 feet per minute. A velocity less than 1 foot per minute is generally considered to be too slow for production operation and a velocity greater than 100 feet per minute can result in signal frequencies beyond the capability of the associated electronic circuits.

Because of the relatively low level of the signals from the coil 16, care should be taken to minimize noise from mechanical vibration and stray electrical fields. Also, it is desirable to maintain the element 10 being scanned at a reasonably constant temperature because of the 1/T relationship of the magnetic susceptibility of the fuel material in the element to temperature. The field produced by magnet 14 should be as high as practical for reasonable signal-to-noise ratios.

The magnetization M or paramagnetic material increases linearly with the applied field H according to the relationship $M = XH$, where X is the susceptibility of the paramagnetic material. A typical mangetization curve for gadolinium additive of about 2.0 weight percent in uranium oxide is illustrated by the dashed line in FIG. 2.

Figure 2:
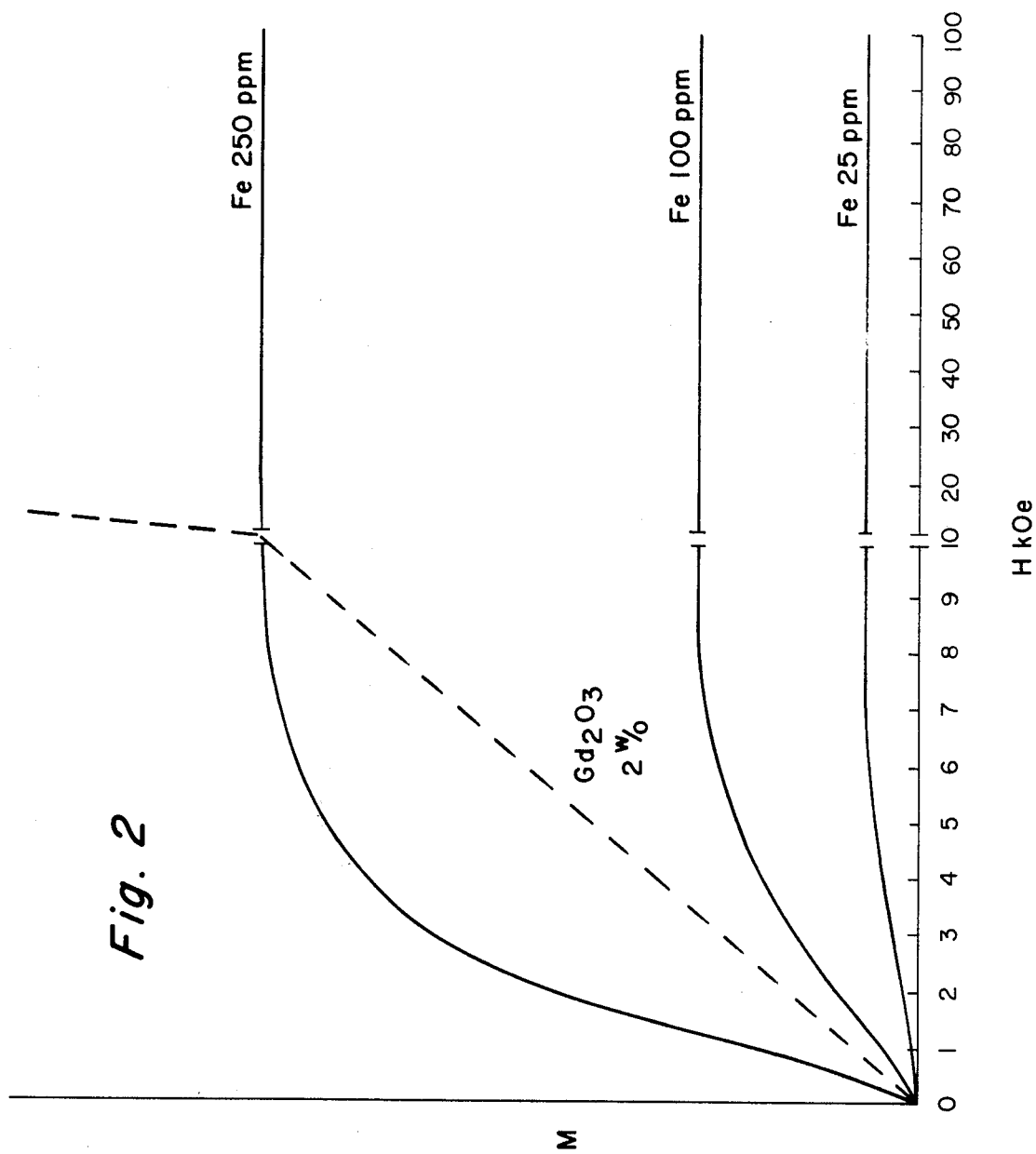
FIG. 2 illustrates typical magnetization curves of gadolinium and ferromagnetic impurities.

However, as an applied field H is increased the susceptibility of the ferromagnetic material decreases and its magnetization M approaches a limit depending upon the amount of material. This is illustrated in FIG. 2 by representative magnetization (M/H) curves of ferromagnetic impurity contents of 25, 100 and 250 ppm in uranium oxide. From these it is seen that ferromagnetic impurities are substantially saturated by fields above about 20 KOe.

Figure 3:
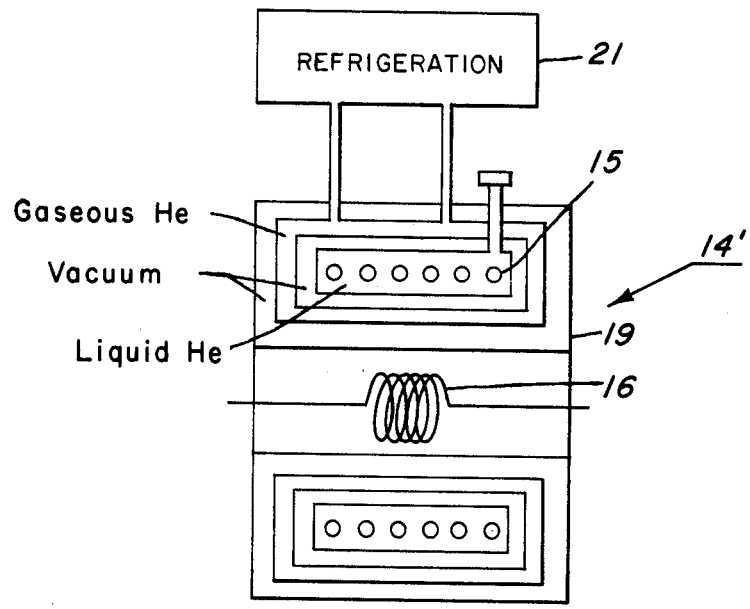
FIG. 3 is a schematic illustration of a superconductive magnet.

Ordinary electromagnets and permanent magnets (as shown in FIG. 1) can provide field strengths up to about 10 KOe. For higher field strengths resort can be had to superconductive solenoids for electormagnets. A superconductive magnet 14' is illustrated in FIG. 3. Such magnets are described, for example, by V. L. Newhouse in "Applied Superconductivity", John Wiley & Sons, Inc., New York, 1964 Typically, the superconductive magnet 14' comprises a coil or core 15 formed of a superconductive material, such as niobium-titanium, connected as a persistent current loop and maintained at superconductive temperature by liquid helium contained in a compartmented, vacuum insulated container or Dewar 19 cooled by a refrigeration unit 21. Such superconductive magnets are available, for example, from Intermagnetics General Corporation, Guilderland, New York.

SECOND EMBODIMENT

In a magnetic field of about 5 KOe a change in ferromagnetic iron impurity content in the order of 100 ppm results in a susceptibility change signal equivalent to a change in gadolinium content of about three weight percent. Thus for accurate determination of the paramagnetic additive content the contribution of an unknown amount of ferromagnetic impurity to the susceptibility change signal must be substantially eliminated.

Figure 4A:
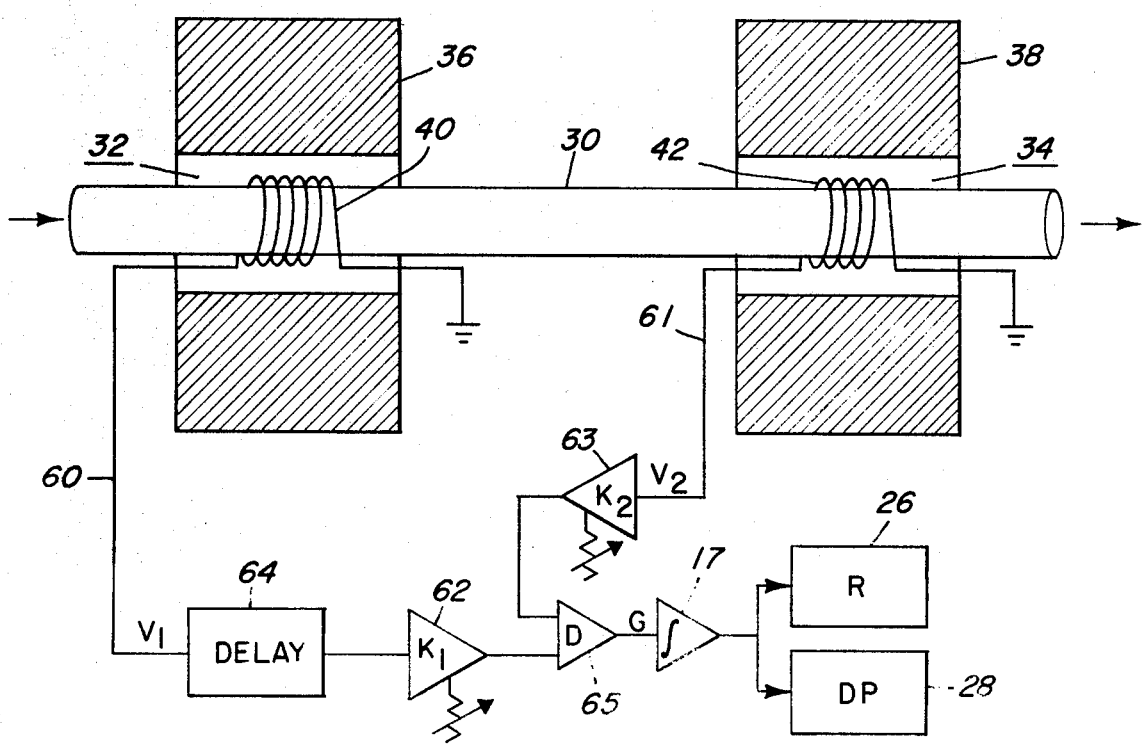
FIG. 4A is a schematic illustration of a pair of magnets and associated circuitry according to a second embodiment of the invention.

Thus shown in FIG. 4A is apparatus for determining the amount of a paramagnetic additive, such as gadolinium, in another paramagnetic material having significantly different paramagnetic susceptibility, such as nuclear fuel, and which contains ferromagnetic impurities, such as iron, of an unknown amount.

In this embodiment a pair of magnets 36 and 38 are arranged in spaced relation with their bores 32 and 34 in axial alignment. The magnets 36 and 38 may be of the type described above as shown in FIGS. 1 or 3 but with different field strengths. For purposes of discussion it will be assumed that the magnet 36 has the greater field strength.

Positioned within the bores of magnets 36 and 38 are respective sensing coils 40 and 42 which may be similar to the coil 16 of FIG. 1. An element 30 containing the fuel material to be examined (including nuclear fuel, a paramagnetic additive and ferromagnetic impurities) is moved at a constant velocity through the sensing coils 40 and 42 whereby changes in susceptibility of the fuel material produce respective output signals $V_1$ and $V_2$ on respective leads 60 and 61.

The signal $V_1$ on lead 60 is applied to a delay 64. The delay 64 delays the signal $V_1$ from coil 40 so that it appears at the output of the delay coincident in time with the signal $V_2$ from the same increment of element 30. The delay 64 is preferably adjustable so that its delay time can be correlated with the velocity of the element 30 through the sensing coils 40 and 42. (A suitable such delay is available, for example, from Reticon Corporation, Sunnyvale, California as shown in their brochure No. 57324).

The delayed signal $V_1$, at the output of delay 64, is applied through a gain-controlled amplifier 62 to one input of a differential amplifier 65 while the signal $V_2$ is applied through a gain-controlled amplifier 63 to the other input of differential amplifier 65.

The gain-controlled amplifiers modify the levels of the signals $V_1$ and $V_2$ in accordance with predetermined constants $K_1$ and $K_2$ of the system whereby (as more fully described hereinafter), the contribution of the ferromagnetic impurity to the signal is substantially eliminated and the difference signal G at the output of differential amplifier 65 is proportional to the amount of the paramagnetic additive.

As in the embodiment of FIG. 1, the additive indicating signal G may be integrated by the integrating amplifier 17 and recorded by a chart or strip recorder 26 and also (or alternatively) applied to a data processing device 28. Alternatively, the signals on leads 60 and 61 may be converted to digital form and applied to a well-known data processing device wherein the functions of the components 62-65 and 17 can be performed in known manner.

The strengths of both magnets 36 and 38 should be high to maximize sensitivity and saturate the iron component. On the otherhand, their strengths are desirably significantly different to provide a practical level of the difference signal G. A ratio of strengths of about two is found practical. For example, the magnet 36 may have a field strength of about 60 KOe and the magnet 38 a field strength of about 30 KOe.

The difference signal G, which is directly proportional to the amount of the paramagnetic additive, is related to the constant $K_1$ and $K_2$ and voltages $V_1$ and $V_2$ as follows:

$$G = K_1 V_1 - K_2 V_2 \quad (1)$$

$K_1$ and $K_2$ are constants of the system which, suitably determined, result in elimination of the contribution to the signal G of the ferromagnetic impurities.

For a given system and system operating conditions, $K_1$ and $K_2$ most readily are determined empirically, for example, in the following manner: At least two test elements 30 are needed, each of which contains an accurately known change in the additive content along its length. (Or a single element could be used having known additive content change at two suitably separated locations along its length.) For accuracy of determination of $K_1$ and $K_2$ the additive changes in the two test segments should be significantly different. For example, the first may have a change in additive content of 2 and the second a change of 6 weight percent gadolinium oxide in uranium oxide.

The first test element is passed through the coils 40 and 42, at the predetermined element velocity of the system, and a first set of voltages $V_1$ and $V_2$, on leads 60 and 61, resulting from the change in additive content in the element is measured. The second test element is then passed through the coils 40 and 42 and a second set of the resulting voltages $V_1$ and $V_2$ is similarly measured. These two sets of numerical values for the signals $V_1$ and $V_2$ and the corresponding known numerical values of the known additive content are inserted in the relationship (1) above. This provides two equations from which numerical values for $K_1$ and $K_2$ can be determined. The gain-controlled amplifiers 62 and 63 then can be adjusted to represent these numerical values of $K_1$ and $K_2$. Accuracy in the determination of $K_1$ and $K_2$ can be improved by using additional test elements of known additive content change.

Figure 4B:
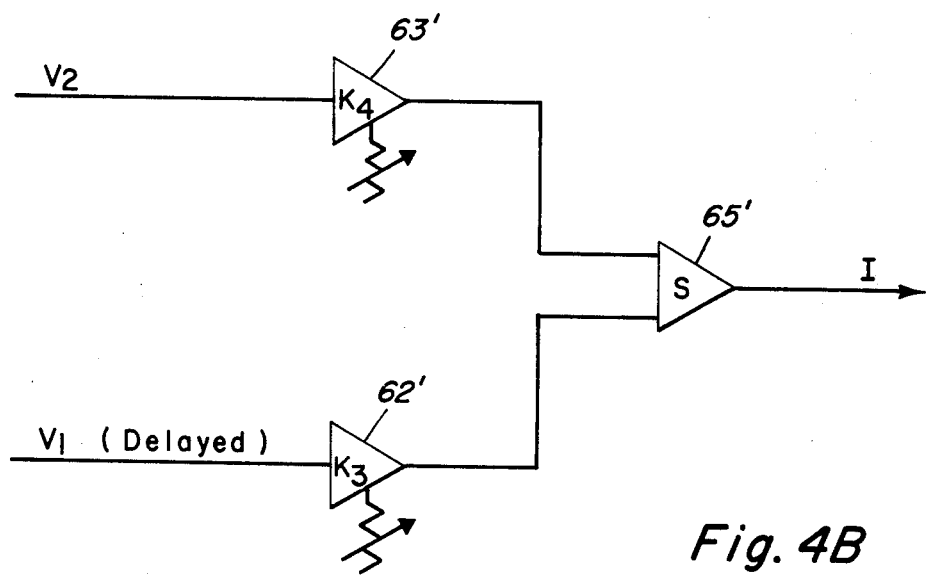
FIG. 4B is a schematic drawing of a circuit for use in the arrangement of FIG. 4A for determining ferromagnetic impurity content.

The apparatus of FIG. 4A can also be used to determine the ferromagnetic impurity content in element 30. As shown in FIG. 4B the output of summing amplifier 65' is a signal I proportional to the ferromagnetic content as follows:

$$I = K_3 V_1 + K_4 V_2 \quad (2)$$

Gain controlled amplifier 62' receives the delayed signal $V_1$ while the gain controlled amplifier 63' receives the signal $V_2$. The constants $K_3$ and $K_4$ can be determined (and the amplifier 62' and 63' adjusted to represent these constants) by use of test elements containing known ferromagnetic content change, in the manner described above for determination of $K_1$ and $K_2$. The relationship (2) is strictly true for cases where the ferromagnetic impurity is saturated, that is, for sufficiently large magnetic fields. For field strengths insufficient to saturate the magnetic impurity, the relationship is more complex and is related to the form of the magnetization curve of the ferromagnetic impurity.

The circuit of FIG. 4B can be substituted for the corresponding circuit (elements 62, 63 and 65) in FIG. 4A or it can be connected in parallel therewith for simultaneous indications of additive and ferromagnetic impurity content. (Also, the function of this circuit can be performed by suitably programmed data processing means.)

Figure 5:
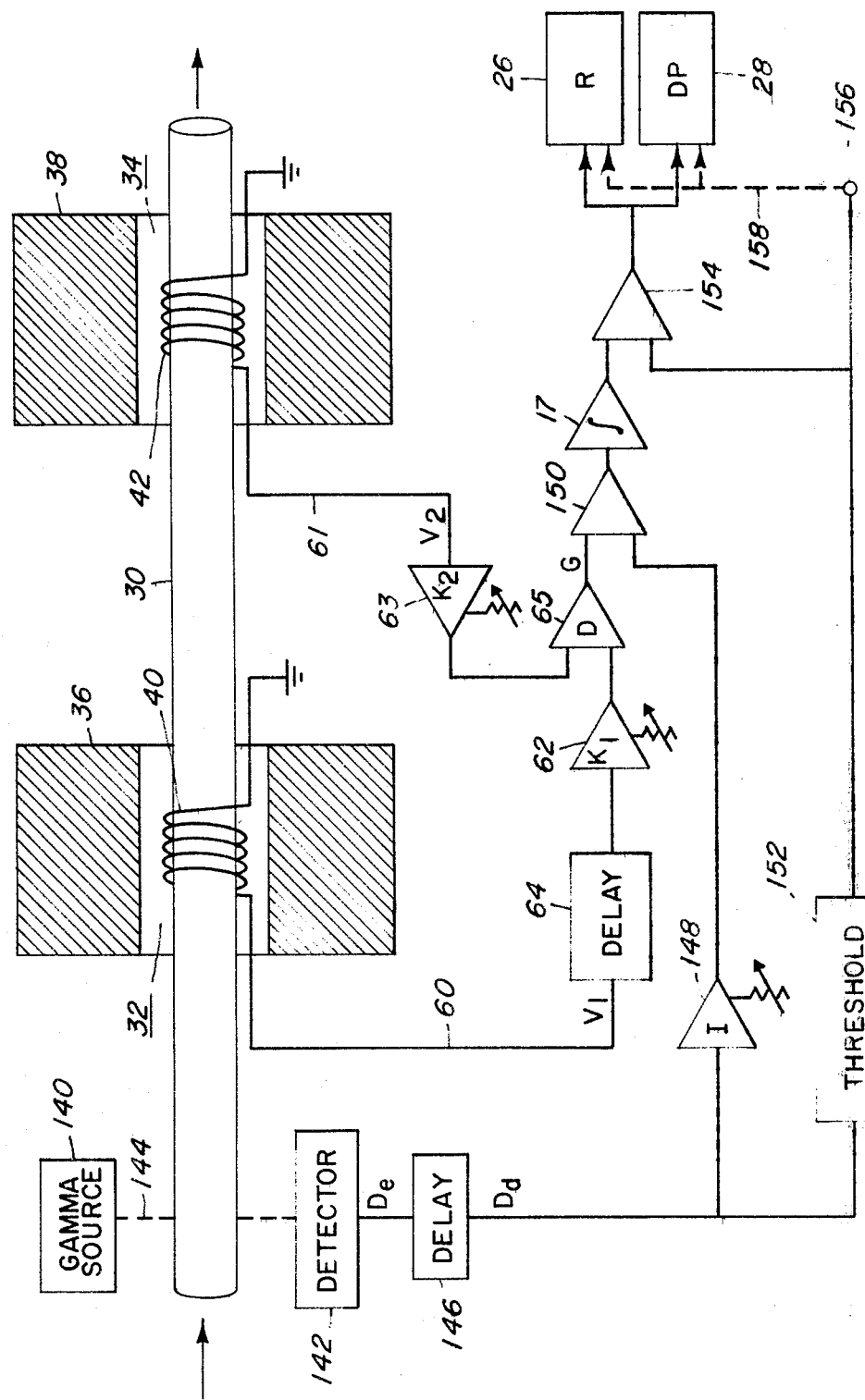
FIG. 5 is a schematic illustration of an embodiment including densitometer means for density correction and void detection.

Shown in FIG. 5 is a version of the invention which includes means for compensating the additive indicating signal for changes in density of the material in the fuel element. Otherwise the basic arrangement and operation is similar to the arrangement and operation of the embodiment of FIG. 4A, and the same reference numbers are applied to the similar elements.

A change of density of the fuel material in element 30 causes a proportional change in the additive indicating signal G since magnetization is directly proportional to mass. Therefore it is desirable to correct the additive indicating signal in accordance with density.

Also, where the fuel material is in the form of pellets, chips from such pellets may be missing or there may be gaps between pellets which constitute large localized changes in fuel material density that induce corresponding voltages in the sensing coils 40 and 42. Such void volumes up to about 5 mm$^3$ are found to have negligible effect on the paramagnetic additive determination. However, for larger void volumes, it is desirable to provide means for preventing a signal due to such a void from being mistaken for a signal due to a change in additive content.

As illustrated in FIG. 5, density of the material in element 30 is sensed by a gamma ray densitometer comprising a suitable gamma beam source 140 and a gamma ray detector 142, positioned on opposite sides of the element 30. The source 140 directs a beam 144 of gamma rays into the element 30. The beam 144 is attenuated in its passage through element 30 in proportion to the density of the material therein and the detector 142 therefore produces an output signal $D_e$ proportional to the material density.

The signal $D_e$ is fed to a delay 146 the delay time of which is selected or adjusted to bring the delayed density signal $D_d$ into time coincidence with the additive indicating signal G (at the output of differential amplifier 65). The signal $D_d$ is applied to an inverting amplifier 148 the output of which is a bias voltage applied to a bias input terminal of a gain controlled amplifier 150 that receives the signal G at its other input terminal. The output signal of amplifier 150 is, therefore, the signal G compensated for density changes of the fuel material.

The density signal $D_d$ is also applied to a threshold circuit 152 which produces an output signal only when its input signal exceeds a predetermined level. The outpt of threshold circuit 152 is connected to a bias input terminal of a gain controlled amplifier 154 which is connected in series between the amplifier 150 and the system output means (recorder 26 and data processing means 28). Thus when the signal $D_d$ exceeds a predetermined level (as caused by a void such as a gap between pellets or a sufficiently large change in density of the fuel material), the threshold circuit 152 applies a cutoff bias to amplifier 154 and thereby prevents the signal from differential amplifier 65 due to such void from reaching the system output means. (The void indicating signal from circuit 152 is also made available at a terminal 156 and may be used to signal and/or record the occurrence of such voids.) For example, this signal may be applied to inputs of the recorder 26 and data processing means 28 as shown by the dashed lead 158.

The threshold circuit 152 may be a well-known Schmitt trigger circuit such as shown, for example, by A. I. Pressman in "Design of Transistorized Circuits for Digital Computers", John F. Rider Publisher, Inc., New York, 1959. Alternatively, the functions of elements 146, 148, 152 and 154 may be performed by suitable data processing means.

The gamma ray source 140 comprises about one curie of radioactive cesium contained in a shielding enclosure with an output port, including collimating means, for directing a narrow bean of gamma rays into the element 30.

The gamma ray detector may comprise a well-known sodium iodide crystal scintillator in combination with a photomultiplier as shown, for example, by W. V. Price in "Nuclear Radiation Detection", McGraw-Hill Book Company, 1964.

Adjustment and calibration of the density compensating and void detection arrangement may be accomplished by use of sample elements 30 containing material having known density changes and voids.

EXAMPLE

The apparatus used was arranged as shown in FIG. 1 (except that no data processing device 28 was used). The magnet 14 was a Gecor (brand) permanent magnet with a field strength of about 5000 Oersted along the axis of its bore 12 of 1.9 cm diameter and 7.9 cm in length. The sensing coil 16 was wound with about 1000 turns of 48-guage copper wire on a suitable tubular form and centered within the bore 12. Amplifier 20 consisted of amplifier models 260 and 234 manufactured by Analog Devices Company connected in series.

A sample fuel rod was constructed with a length of Zircaloy-2 tubing containing an arrangement of uranium oxide fuel pellets of predetermined $Gd_2O_3$ and iron content. This sample fuel rod was guided through the coil 16 at a speed of about ten feet per minute. The voltage produced by coil 16 from the zone-to-zone changes in gadolinia and iron content were recorded by recorder 26 which was a Bell and Howell Datagraph 5-144 oscillographic recorder.

Figure 6:
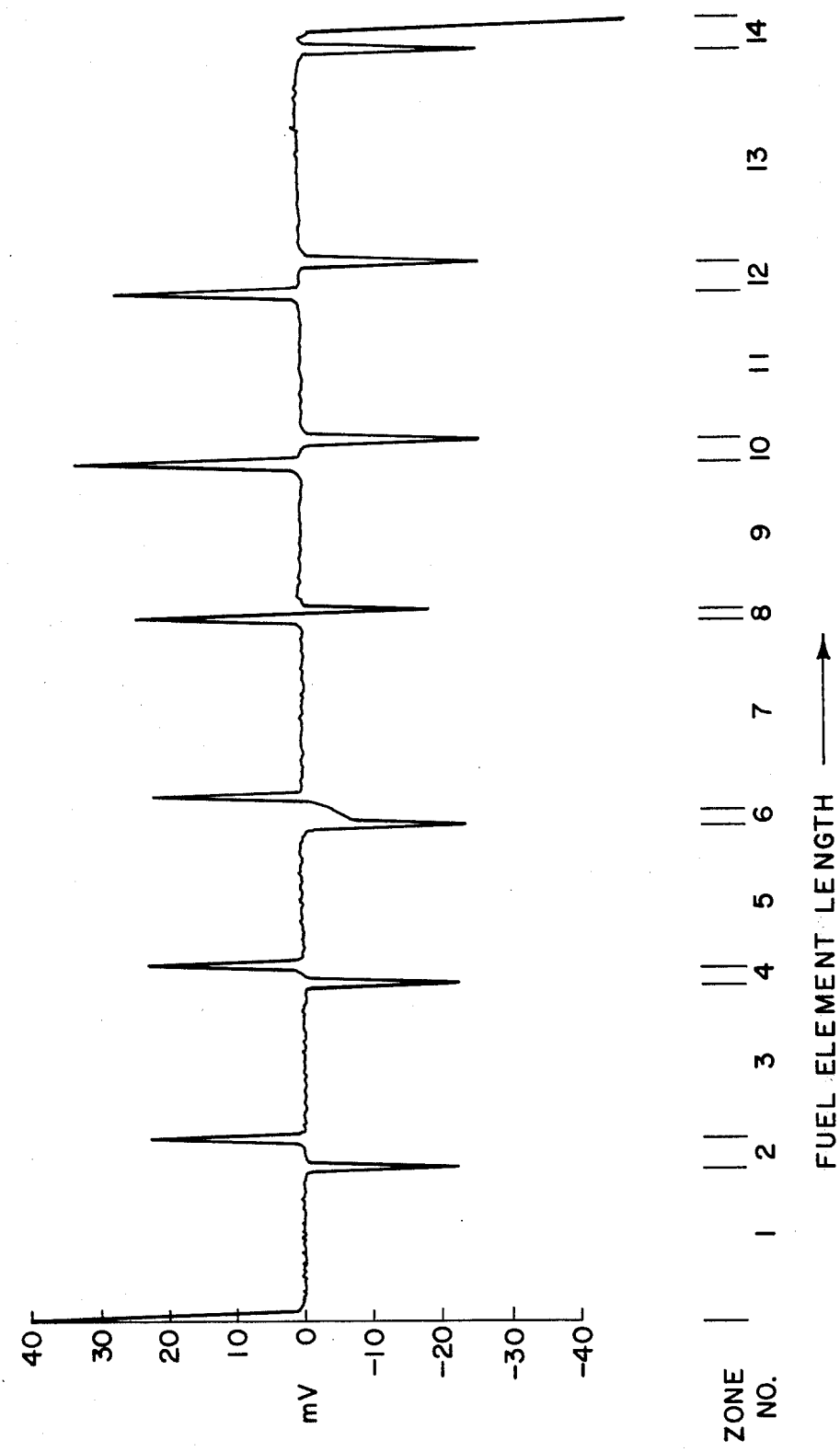
FIG. 6 is a graph of the signals from a sample element tested with the arrangement of FIG. 1.

FIG. 6 is a graph of the non-integrated voltages obtained along the length of the sample fuel rod with respect to the zones thereof. FIG. 7 is a chart which identifies the zones of the sample fuel rod, the number of pellets in each zone and the gadolinia and iron content thereof. Also given is the peak voltage obtained at the zone interfaces. The data of FIG. 7 were analyzed to determine the separate effects of changes in gadolinia and iron content. For the experimental condition, it was determined that a 1 weight percent change in $Gd_2O_3$ content provides a 25 mV peak voltage while a 50 ppm change in Fe content provides a 14 mV peak voltage. It was noted that not all of the iron was ferromagnetic. This was a consequence of iron alloy constituents and of the heat treatment process used in preparing the fuel pellets.

In another example, the apparatus was functional equivalent of the arrangement of FIG. 5. The magnets 36 and 38 were superconductive solenoids, the magnets providing fields of about 70 and 35 KOe, respectively. The magnets 36 and 38 were contained in the same insulating container or Dewar with the sensing coils 40 and 42 being spaced apart about 25 cm.

This apparatus was used to scan an example fuel element clad with zirconium alloy with an outside diameter of about 1 cm and containing a column of fuel pellets of about 3.5 m in length. The fuel element was passed through the sensing coils 40 and 42 at a velocity of about 15 feet per minute. The fuel was arranged in the fuel element in 17 zones of different lengths and with different gadolinium content. The results of a scan of this fuel element are shown in FIG. 8 wherein the gadolinium indicating signal is expressed as weight percent gadolinium. The density of the fuel material in the various zones, as determined by the gamma ray densitometer, is also given, as is the target or intended gadolinium weight percent.

While the invention has been described herein as applied to the determination of paramagnetic additive and ferromagnetic impurity content of nuclear fuel, the invention can be used for other analogous purposes, such as determining the ferromagnetic material content in a base paramagnetic material and/or the paramagnetic additive content in a base paramagnetic material where the paramagnetic susceptibilities of the additive and the base material are sufficiently different.

What is claimed is:

1. A method of detecting a paramangetic additive in a base paramagnetic material having an appreciably different susceptibility and containing ferromagnetic impurities comprising the steps of:
   (a) establishing first and second direct current magnetic fields of different strengths;
   (b) disposing in each magnetic field respective first and second inductive means for producing signals indicative of changes in susceptibility of material moved adjacent thereto;
   (c) moving said material through said magnetic fields and adjacent said first and second inductive means in sequence, the strengths of said magnetic fields in the regions adjacent said first and second inductive means being sufficient to substantially saturate said ferromagnetic impurities throughout each incremental portion of said material; and
   (d) processing the signals from said first and second inductive means to provide signals representative of the differential susceptibility changes of said material in the two magnetic fields.

2. A method for detecting a paramagnetic additive in a base paramagnetic material having an appreciably different susceptibility comprising the steps of:
   (a) establishing first and second direct current magnetic fields of different strengths greater than about 1000 Oersteds;
   (b) disposing in each magnetic field respective first and second inductive means for producing signals indicative of changes in susceptibility of material moved adjacent thereto;
   (c) moving said material adjacent said first and second inductive means in sequence; and
   (d) processing the resulting signals from said first and second inductive means wherein said processing includes adjusting the magnitude of the signals from said first and second inductive means in accordance with respective predetermined constants $K_1$ and $K_2$ and determining the difference in magnitude of the adjusted first and second signals from the same incremental portions of said material to thereby provide additive indicating signals indicative of the additive content of said material for each incremental portion thereof.

3. The method of claim 2 including comparing said additive indicating signals to similar signals obtained from a standard material containing known additive content.

4. A method according to claim 2 in which said magnetic fields are of strengths in the range of 1,000 to 100,000 Oersteds.

5. A method according to claim 2 in which the strength of one of the magnetic fields is about twice the strength of the other magnetic field.

6. A method according to claim 2 in which said magnetic fields are of strengths greater than 10,000 Oersteds and are established by superconductive magnets.

7. A method according to claim 2 in which said material is moved adjacent said first and second inductive means at a constant rate.

8. A method according to claim 7 in which the rate is from about 1 to about 100 feet per minute.

9. A method according to claim 2 in which said material is in the form of powder.

10. A method according to claim 2 in which said material is in the form of pellets.

11. A method according to claim 2 in which said material is in the form of pellets and the pellets are enclosed in a cladding, forming a nuclear fuel element.

12. A method according to claim 2 in which said material is a compound selected from the group consisting of compounds of uranium, plutonium, thorium and mixtures thereof.

13. A method according to claim 2 in which said material is comprised of an oxide compound.

14. A method according to claim 2 in which said material is comprised of a carbide compound.

15. A method according to claim 2 in which said material is comprised of a nitride compound.

16. A method according to claim 2 in which the additive is comprised of gadolinium.

17. A method for detecting a paramagnetic additive in a base paramagnetic material having an appreciably different susceptibility comprising the steps of:
   (a) establishing first and second direct current magnetic fields of different strengths greater than about 1000 Oersteds;
   (b) disposing in each magnetic field respective first and second inductive means for producing signals indicative of changes in susceptibility of material moved adjacent thereto;
   (c) moving said material adjacent said first and second inductive means in sequence; and
   (d) processing the resulting signals from said first and second indicative means to provide an additive indicating signal indicative of the content of said paramagnetic additive of said material; and
   (e) determining the density of said incremental portions of said material and adjusting said additive indicating signal in accordance with said density.

18. A method for detecting the ferromagnetic impurity content in a base paramaagnetic material comprising the steps of:
   (a) establishing first and second direct current magnetic fields of different strengths greater than about 1000 Oersteds;
   (b) disposing in each magnetic field respective first and second inductive means for producing signals indicative of changes in susceptibility of material moved adjacent thereto;
   (c) moving said material adjacent said first and second inductive means in sequence; and
   (d) processing the resulting signals from said first and second inductive means wherein said processing includes adjusting the magnitude of the signals from said first and second inductive means in accordance with respective constants $K_3$ and $K_4$ and determining the sum of the magnitudes of the adjusted first and second signals from the same incremental portions of said material to thereby provide a ferromagnetic indicating signal indicative of the ferromagnetic impurity content of said material for each incremental portion thereof.

19. Apparatus for determining the paramagnetic additive content of an elongated element of a base paramagnetic material having a susceptibility appreciably smaller than the susceptibility of said additive, comprising the combination of: spaced first and second direct current magnets having bores in axial alignment and providing magnetic fields of different strengths greater than about 1000 Oersteds; first and second sensing coils positioned, respectively, within the bores of said magnets; means for passing said element through said first and second sensing coils in sequence whereby first and second signals are produced by said coils in response to changes in susceptibility of incremental portions of said elements; and means for processing said signals including means responsive to the density of the material of said element for modifying said signals in accordance with the density of said incremental portions of said element.

20. Apparatus of claim 19 wherein said magnetic fields have strengths in the range of 1000 to 100,000 Oersteds.

21. Apparatus of claim 19 wherein the strength of one of the magnetic fields is about twice the strength of the other magnetic field.

22. Apparatus of claim 19 wherein the strengths of said magnetic fields are greater than 10,000 Oersteds and are established by superconductive magnets.

23. Apparatus of claim 19 wherein said base paramagnetic material is nuclear fuel and said additive is gadolinium.

24. Apparatus for determining the paramagnetic additive content of an elongated element of a base paramagnetic material having a susceptibility appreciably smaller than the susceptibility of said additive, and containing ferromagnetic impurities comprising the combination of: spaced first and second direct current magnets having bores in axial alignmen and providing magnetic fields of different strengths greater than about 1000 Oersteds; first and second sensing coils positioned, respectively, within the bores of said magnets; means for passing said element through said first and second sensing coils in sequence whereby first and second signals are produced by said coils in response to changes in susceptibility of incremental portions of said element; and means for processing said signals including means for determining a signal G in accordance with:

$$G = K_1 V_1 - K_2 V_2$$

where G is proportional to the additive content of an incremental portion of said element, $K_1$ and $K_2$ are predetermined constants of the system, and $V_1$ and $V_2$ are said first and second signals, respectively, produced from said incremental portion of said element.

25. Apparatus of claim 24 wherein said constants $K_1$ and $K_2$ are determined from at least two standard elements of known different additive content.

26. Apparatus of claim 24 including a delay circuit for receiving the signal $V_1$ and providing the signal $V_1$ at its output in time coincidence with the signal $V_2$ from the same incremental portion of said element; respective circuits receiving the delayed signal $V_1$ and the signal $V_2$ and modifying them in accordance with the constants $K_1$ and $K_2$; and a differential amplifier receiving the modified signals $V_1$ and $V_2$ and producing the difference signal G.

27. Apparatus of claim 24 including means responsive to the density of said incremental portion of said element for modifying said signal G.

28. Apparatus according to claim 24 including means for recording the signal G produced from each successive incremental portion of said element.

29. Apparatus of claim 28 including means for comparing the signal G to stored signals from standard elements of known additive content.

30. Apparatus of claim 19 including means for detecting voids in the material of said element.

31. Apparatus of claim 19 wherein said magnets are superconductive magnets providing magnetic fields of strengths greater than 10,000 Oersteds.

32. Apparatus of claim 19 wherein said material comprises a series of pellets and including means for detecting gaps greater than a predetermined width between said pellets.

33. Apparatus for determining the ferromagnetic impurity content of an elongated element of a base paramagnetic material, comprising the combination of: spaced first and second direct current magnets having bores in axial alignment and providing magnetic fields of different strengths greater than about 1000 Oersteds; first and second coils positioned, respectively, within the bores of said magnets; means for passing said element through said first and second sensing coils in sequence whereby first and second signals are produced by said coils in response to changes in susceptibility of incremental portions of said element; and means for processing said signals including means for determining a signal I in accordance with:

$$I = K_3 V_1 + K_4 V_2$$

where I is proportional to the ferromagnetic impurity content of an incremental portion of said element, $K_3$ and $K_4$ are predetermined constants of the system, and $V_1$ and $V_2$ are said first and second signals, respectively, produced from said incremental portion of said element.

* * * * *